(12) United States Patent
Veinberg et al.

(10) Patent No.: US 9,102,615 B2
(45) Date of Patent: Aug. 11, 2015

(54) N-CARBAMOYLMETHY1-4-(R)-PHENYL-2-PYRROLIDINONE, METHOD OF ITS PREPARATION AND PHARMACEUTICAL USE

(75) Inventors: Grigory Veinberg, Riga (LV); Maksim Vorona, Riga (LV); Liga Zvejniece, Riga (LV); Aleksandrs Chernobrovijs, Olaine (LV); Ivars Kalvinsh, Ikskile (LV); Ligita Karina, Riga (LV); Maija Dambrova, Riga (LV)

(73) Assignee: Joint Stock Company (JSC) "OLAINFARM" (LV)

( * ) Notice: Subject to any disclaimer, the term of this patent is extended or adjusted under 35 U.S.C. 154(b) by 522 days.

(21) Appl. No.: 12/226,332

(22) PCT Filed: Mar. 15, 2007

(86) PCT No.: PCT/EP2007/052424
§ 371 (c)(1),
(2), (4) Date: Dec. 29, 2008

(87) PCT Pub. No.: WO2007/104780
PCT Pub. Date: Sep. 20, 2007

(65) Prior Publication Data
US 2010/0022784 A1    Jan. 28, 2010

(30) Foreign Application Priority Data
Mar. 16, 2006   (LV) ........................................ P-06-45

(51) Int. Cl.
*C07D 207/27*    (2006.01)
(52) U.S. Cl.
CPC .................................. *C07D 207/27* (2013.01)

(58) Field of Classification Search
CPC ...................................................... C07D 207/27
See application file for complete search history.

(56) References Cited

U.S. PATENT DOCUMENTS 6,784,197 B2 *    8/2004   Differding et al. ........... 514/365

OTHER PUBLICATIONS

Spektor et al. (Pharmaceutical Chemistry Journal, (1996), 30 (8); p. 489-490).*
Spektor et al. (Intl. J. Androl., 20:347-355 (1977).*
Berestovitskaya et al. (IZVESTIA: Herzen University Journal of Humanities and Sciences, (2002) vol. 2 (4).*
Carphedon Trademark (publication date 1990).*
Williams et al. (Foye's Principles of Medicinal Chemistry, 2002, 5th Ed., p. 50).*
USFDA—"Development of New Stereoisomeric Drugs" May 1, 1992, p. 1-4.*
Marie-Luse Weischer, et al Eine einfache Versuchsanordnung zur quantitativen Beurteilung von Motilitat und Neugierverhalten bei Mausen, Psychopharmacology 50, 275-279 (1976).
Porsolt, et al, Behavioural Despair in Mice: A Primary Screening Test for antidepressants, Arch. Int. Pharmacodyn, 229, 327-336(1977).
Marie-Luse Weischer, et al Eine einfache Versuchsanordnung zur quantitativen Beurteilung von Motilitat und Neugierverhalten bei Mausen, Psychopharmacology 50, 275-279 (1976) (English translation).

* cited by examiner

*Primary Examiner* — Valerie Rodriguez-Garcia
(74) *Attorney, Agent, or Firm* — Caesar Rivise, PC

(57) ABSTRACT

The invention relates to the R-enantiomer of N-carbamoylmethyl-4-phenyl-2-pyrrolidinone (R-Carphedon) of pharmacological value. The method of its preparation includes the N-alkylation of 4(R)-phenyl-2-pyrrolidinone with ethyl bromoacetate in the presence of a strong base and the treatment of intermediate N-ethoxycarbonylmethyl-4(R)-phenyl-2-pyrrolidinone with ammonia.

6 Claims, No Drawings

N-CARBAMOYLMETHYL-4-(R)-PHENYL-2-PYRROLIDINONE, METHOD OF ITS PREPARATION AND PHARMACEUTICAL USE

BACKGROUND OF THE INVENTION

The invention relates to the discovery of the biologically active R-enantiomer of N-carbamoylmethyl-4-aryl-2-pyrrolidinone and easy and effective method of its preparation.

It is known that humans in a stress situation or under psycho-emotional strain exhibit irrational and inadequate forms of behavior, disorders of mental capacity, declined speed of reaction, and increased number of erroneous decisions etc.

Therefore discovery of pharmaceuticals abating and preventing the effect of a stress factor is of substantial importance. For this purpose the nootropic GABA derivatives: Phenibut and Baclofen are applied, even though their use is followed by drowsiness, depression, dizziness, lowered psychomotor reactions etc.

In comparison to GABA derivatives another agent widely used for this purpose N-carbamoylmethyl-4-aryl-2-pyrrolidinone (Carphedon, INN) could be regarded as a much more perspective psycho-stimulator due to the less pronounced side effects.

The R- and S-enantiomeric forms of Carphedon and their pharmacologic properties are not known. The pharmacologic properties of only the racemic Carphedon are published today and there is no data concerning possible differences of pharmacological properties for its separate R- and S-enantiomers. The absence of this highly important information also does not allow to adequately estimate the real pharmaceutical potential of Carphedon already used in medicine, because in reality it is represented by a mixture of R- and S-enantiomers, which may exhibit different pharmacologic properties.

In the present invention we have developed methods for preparation of pure R- and S-Carphedon and unexpectedly discovered that R-Carphedon as an antidepressant, analgesic, muscle relaxant and psycho-stimulating compound is more effective than the racemic Carphedon or S-Carphedon.

SUMMARY AND DETAILED DESCRIPTION

The invention relates to the R-enantiomer of 4-phenyl-1-pyrrolidine acetic acid amide. More particularly, the invention relates to N-carbamoylmethyl-4(R)-phenyl-2-pyrrolidinone of the formula:

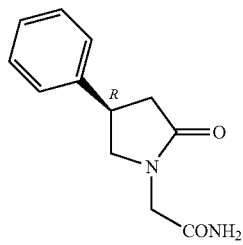

a new chemical compound of pharmacological value and a method of its production.

DETAILED DESCRIPTION OF THE INVENTION

As we have discovered, the preparation of R-Carphedon 4 the same as S-Carphedon 4a can be easily achieved by the means of the N-alkylation of available 4(R)-phenyl-2-pyrrolidinone (1) or 4(S)-phenyl-2-pyrrolidinone (1a) with ethyl bromoacetate (2) in the presence of a strong base and by the following transformation of ethoxycarbonyl group in the intermediate 2-pyrrolidinones 3 and 3a into carbamoyl function by the treatment with ammonia.

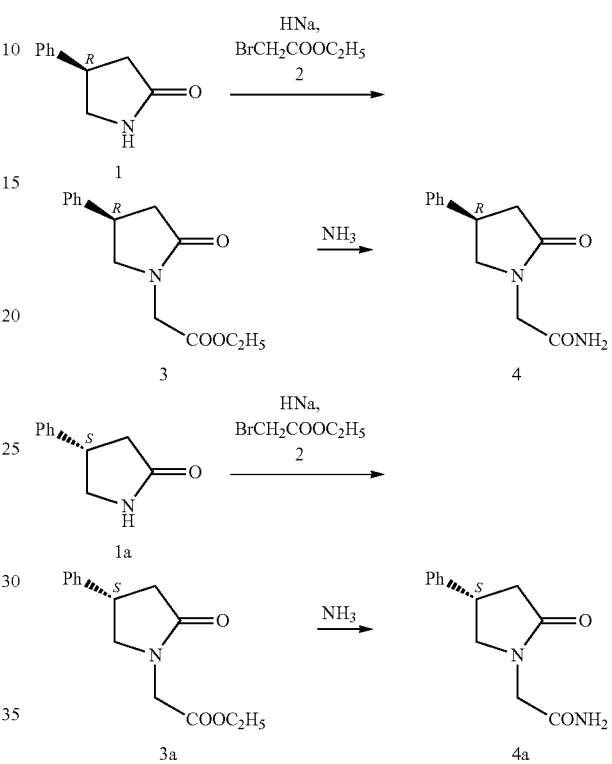

Following examples illustrate the synthetic part of invention.

Example 1

N-Carbamoylmethyl-4(R)-phenyl-2-pyrrolidinone (4)

The solution of 4(R)-phenyl-2-pyrrolidinone (1) (345 mg, 2.14 mM) in 1,4-dioxane (30 ml) was added to the suspension of sodium hydride (56 mg, 2.35 mM) in 1,4-dioxane (30 ml). The mixture was heated at 80÷90° C. during 30 min and then cooled to room temperature. Ethyl bromoacetate (393 mg, 2.37 mM) was added and the reaction mixture was refluxed at 110÷120° C. for 6 hours. Obtained mixture was concentrated under reduced pressure. Residue was purified by column chromatography on silicagel with ethylacetate-hexane mixture 1:1, giving N-ethoxycarbonylmethyl-4(R)-phenyl-2-pyrrolidinone (3) (338 mg, 64%). $[\alpha]_D^{20}=+4.6°$ (c=3; MeOH). $^1$H NMR (CDCl$_3$), δ: 1.28 (3H, t, CH$_2$CH$_3$); 2.59 (1H, d, d, 3-CH$_2$); 2.87 (1H, d, d, 3-CH$_2$); 3.54 (1H, t, 5-CH$_2$); 3.64 (1H, quintet, 4-CH); 3.83 (1H, t, 5-CH$_2$); 4.11 (2H, s, NCH$_2$CO); 4.20 (2H, q, CH$_2$CH$_3$); 7.20-7.39 (5H, m, C$_6$H$_5$).

The solution of N-ethoxycarbonylmethyl-4(R)-phenyl-2-pyrrolidinone (3) (250 mg, 1.01 mM) in methanol (30 ml) saturated by stream of gaseous ammonia for 5 hours. Reaction mixture was concentrated under reduced pressure and the residue was purified by column chromatography with ethylacetate-hexane mixture 1:1 silicagel giving N-carbamoylmethyl-4(R)-phenyl-2-pyrrolidinone (4a) (187 mg, 85%). M.p.

107.5-108° C. $[\alpha]_D^{20}$=+8.5° (c=3, MeOH). $^1$H NMR (CDCl$_3$), δ: 2.61 (1H, d, d, 3-CH$_2$); 2.87 (1H, d, d, 3-CH$_2$); 3.54 (1H, t, 5-CH$_2$); 3.66 (1H, quintet, 4-CH); 3.89 (1H, t, 5-CH$_2$); 4.00 (2H, s, NCH$_2$CO); 5.68 and 6.21 (1H and 1H, br.s and br.s, NH$_2$); 7.20-7.40 (5H, m, C$_6$H$_5$).

Example 2

N-Carbamoylmethyl-4(S)-phenyl-2-pyrrolidinone (4a)

Substituting pyrrolidinone 1 in Example 1 by 4(S)-phenyl-2-pyrrolidinone (1a) S-enantiomeric N-carbamoylmethyl-4 (S)-phenyl-2-pyrrolidinone (4a) was obtained. $[\alpha]_D^{20}$=−8.3° (c=3, MeOH). $^1$H NMR (CDCl$_3$), δ: 2.61 (1H, d, d, 3-CH$_2$); 2.87 (1H, d, d, 3-CH$_2$); 3.54 (1H, t, 5-CH$_2$); 3.66 (1H, quintet, 4-CH); 3.89 (1H, t, 5-CH$_2$); 4.00 (2H, s, NCH$_2$CO); 5.68 and 6.21 (1H and 1H, br.s and br.s, NH$_2$); 7.20-7.40 (5H, m, C$_6$H$_5$).

According to the invention, we have performed the comparative investigation of antidepressant, muscle relaxant, locomotor and analgesic activities for R- and S-enantiomers of N-carbamoylmethyl-4-aryl-2-pyrrolidinone and compared with those of the racemic one (Carphedon) (Table 1-3). We have unexpectedly discovered, that R-Carphedon possesses more pronounced desired pharmacological properties comparing with S-Carphedon.

The data presented in Table 1 demonstrate an excellent antidepressant activity of R-enantiomer of Carphedon using the standard Porsolt forced swim test (FST). After the preliminary treatment with R-Carphedonl, the animals did not spent any time immobile. Also in the case of animals treated with racemic Carphedon, the immobility period was significantly shorter. Contrary to that, mice in the control and S-Carphedon groups demonstrated characteristic behavior for FST test conditions registered as an immobilization in response to stress factor.

Similar advantage of R-Carphedon in comparison to S-Carphedon and racemate was observed in experiments characterizing the motor activity of mice in the standard open field test (Table 2). The i.p. administration of the test compounds in equal 50 mg/kg doses caused prolonged and stable increase in animal activity in the case of R-Carphedon, which at the end of the 120 min observation period was about two times higher than activity caused by S-Carphedonl.

The data presented in Table 3 show that equal muscle relaxant activity and analgesic effect of tested compounds was achieved by the lower dosages of R-Carphedon than the same of S-Carphedon.

TABLE 1

Antidepressant properties of test compounds according to Porsolt* forced swim test (FST)**

| Test substance | Immobilization time, sec* |
|---|---|
| Control | 215 ± 10 |
| Carphedon | 35 ± 12[##] |
| R-Carphedon | 0[##] |
| S-Carphedon | 110 ± 12[#] |

*R. D. Porsolt, et. al., Arch. Intern. Pharmacodynamie, 1977, vol. 229, p. 327-336
**i.p. administration of compounds 1 hour before the test in male ICR mice in the dosage of 100 mg/kg
[#]P > 0.05 vs control
[##]P > 0.001 vs control

TABLE 2

Characteristics of locomotor activity* after i.p. administration of tested compounds in male ICR mice in dosage of 50 mg/kg*

| Test substance | Horizontal activity counts (min) | | | Vertical activity counts (min) | | | Exploratory activity counts (min) | | |
|---|---|---|---|---|---|---|---|---|---|
| | 30 | 60 | 120 | 30 | 60 | 120 | 30 | 60 | 120 |
| Control | 47.3 ± 2.1 | 25.5 ± 1.7 | 21.6 ± 1.8 | 10.3 ± 1.1 | 7.5 ± 0.9 | 4.1 ± 0.7 | 18.7 ± 1.9 | 16.8 ± 1.8 | 11.3 ± 1.3 |
| Carphedon | 72.3[#] ± 6.0 | 61.4[#] ± 6.7 | 49.4[#] ± 5.8 | 12.3 ± 4.0 | 10.9 ± 2.5 | 7.9 ± 2.0 | 14.8 ± 3.0 | 19.1 ± 4.8 | 17.8 ± 2.8 |
| R-Carphedon | 77.9[#] ± 5.7 | 80.4[#] ± 6.5 | 78.4[#] ± 7.1 | 10.0 ± 1.5 | 12.5 ± 3.2 | 11.6 ± 4.0 | 15.5 ± 2.9 | 16.4 ± 3.6 | 17.8 ± 4.7 |
| S-Carphedon | 56.3 ± 5.7 | 43.3[#] ± 6.6 | 36.4 ± 7.1 | 7.0 ± 1.6 | 7.0 ± 2.8 | 4.9 ± 1.7 | 5.5[#] ± 1.5 | 7.8 ± 4.2 | 11.5 ± 2.8 |

*M. L. Weischer, Psychopharmacology 1976; 50; 275
[#]P < 0.05 ANOVA test followed Studen's t-test.

TABLE 3

Effective dosages of test compounds responsible for the same muscle relaxant activity[1] and analgesic effect[2] in male ICR mice.

| | ED$_{50}$ (mg/kg)* | | | |
|---|---|---|---|---|
| Test substance | Muscle relaxant activity | | | Analgesic effect |
| | Chimney test | Traction | Rota rod | Hot plate |
| R-Carphedon | 199 ± 38 | 456 ± 122 | 193 ± 26 | 10 ± 42 |
| S-Carphedon | 286 ± 78 | 548 ± 75 | 459 ± 87 | 50 ± 63 |

*i.p. administration in dosages 50; 100; 250 and 500 mg/kg
[1]N. W. Dunham, et. al., J. Am. Pharm. Assoc., 46: 208, 1957.
[2]N. B. Eddy, D. Leimbach, J. Pharmacol. Experimental Therapy, 1953, vol. 107, N 3, p. 358-393.

The obtained results prove the high therapeutic value for R-Carphedon exceeding the same one for racemic Carphedon, because pharmaceutical properties of the latter are negatively affected by the presence of S-Carphedon, which characterizes by lower and in some experiments by considerably weaker activity.

We claim:

1. Pure N-carbamoylmethyl-4(R)-phenyl-2-pyrrolidinone (I), separate from the S-enantiomer, with nootropic activity:

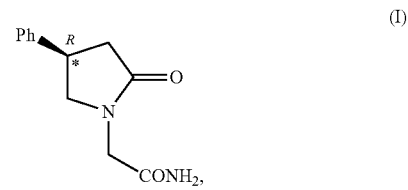

(I)

wherein * marks chiral carbon atom.

2. A method for the preparation of the compound of claim 1 by the N-alkylation of 4(R)-phenyl-2-pyrrolidinone with ethyl bromoacetate followed by carbamoylation of intermediate N-ethoxycarbonylmethyl-4(R)-aryl-2-pyrrolidinone with ammonia.

3. N-carbamoylmethyl-4(R)-phenyl-2-pyrrolidinone, separate from the S-enantiomer, with psycho-stimulating activity, prepared by the N-alkylation of 4(R)-phenyl-2-pyrrolidinone with ethyl bromoacetate following by carbamoylation of intermediate N-ethoxycarbonylmethyl-4(R)-aryl-2-pyrrolidinone with ammonia.

4. Pure N-carbamoylmethyl-4(R)-phenyl-2-pyrrolidinone (I), separate from the S-enantiomer, with psycho-stimulating activity:

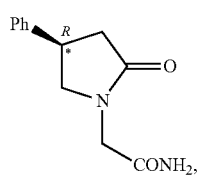

(I)

wherein * marks chiral carbon atom, prepared by the N-alkylation of 4 (R)-phenyl-2-pyrrolidinone with ethyl bromoacetate followed by carbamoylation of intermediate N-ethoxycarbonylmethyl-4(R)-aryl-2-pyrrolidinone with ammonia.

5. A pharmaceutical composition comprising pure N-carbamoylmethyl-4(R)-phenyl-2-pyrrolidinone (I), separate from the S-enantiomer, with psycho-stimulating activity.

6. The pharmaceutical composition of claim 5, wherein the pure N-carbamoylmethyl-4(R)-phenyl-2-pyrrolidinone (I), separate from the S-enantiomer, is prepared by the N-alkylation of 4(R)-phenyl-2-pyrrolidinone with ethyl bromoacetate followed by carbamoylation of intermediate N-ethoxycarbonylmethyl-4(R)-aryl-2-pyrrolidinone with ammonia.

* * * * *